United States Patent [19]

Saville

[11] Plant 4,457

[45] Aug. 28, 1979

[54] ROSE PLANT

[76] Inventor: F. Harmon Saville, 58 Hammond St., Rowley, Mass. 01969

[21] Appl. No.: 955,222

[22] Filed: Oct. 27, 1978

[51] Int. Cl.[2] ..... A01H 5/00

[52] U.S. Cl. ..... Plt./8

[58] Field of Search ..... Plt./8

*Primary Examiner*—Robert E. Bagwill

*Attorney, Agent, or Firm*—Vincent G. Gioia

[57] ABSTRACT

A new miniature rose of deep yellow coloring which lightens slightly upon aging.

1 Drawing Figure

1

The present invention relates to a new and distinct variety of rose plant of the miniature rose class, which was originated by my crossing as seed parent the rose known as "Arthur Bell" and the rose known as "Yellow Jewel" as pollen parent.

Among the novel characteristics possessed by this new variety which distinguish it from its parents and all other varieties of which I am aware are: (1) beautiful yellow colored blooms of good form borne primarily singly to a stem in a manner typical of hybrid tea plants and also blooming on long basal canes, (2) flowers of relatively strong sweet fragrance and (3) a well branched, very compact, growing plant normally with glossy sculptured foliage similar to its parent, the floribunda Arthur Bell. Asexual reproduction by budding of the new variety as performed in Essex County, Mass., shows that the foregoing and other distinguishing characteristics come true to form and are established and transmitted through succeeding propagations.

The new and improved rose variety which I have developed is an unusually fine miniature rose of strong yellow coloring, singly-borne blooms of high centered, hybrid-tea like form are delightfully displayed on an extremely compact plant of attractive foliage. The flowers are unusually well formed, for a yellow miniature rose and the plant displays flowers of deep yellow general tonality since the blooms lighten only slightly upon aging. An additional attractive feature is the unusually strong fragrance for a miniature rose.

The accompanying drawing shows typical specimens of the vegetative growth and flowers of the new variety in different stages of development and as depicted in color as nearly true as it is reasonably possible to make the same in color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "15A" is plate 15A of the Royal Horticultural Society Color Chart.

Parentage: Seedling.

*Seed parent.*—"Arthur Bell".

*Pollen parent.*—"Yellow Jewel".

Class: Miniature.

The following observations are made of specimens grown in Essex County, Mass., during the month of September.

2

1. FLOWER

Blooming habit: Continuous.

A. Bud (1) *Size.*—Medium.

(2) *Form.*—Ovate.

(3) *Color.*—When sepals first divide — 15A. When petals begin to unfurl — 15B. When half-blown: 14C. Reverse side of petals — 15C.

(4) *Sepals.*—Relatively smooth, same length as bud or slightly longer, reflex downward as flower opens.

(5) *Peduncle.*—Length — about ¾ to 1 inch, good proportion to bloom. Aspect — straight. Strength — erect, strong. Color — 145A.

Bloom:

(1) *Size.*—Average size when fully expanded — about 1½ to 1¾ inches.

(2) *Borne.*—Primarily singly.

(3) *Form.*—Sometimes high centered, sometimes cupped, becoming flat upon opening.

(4) *Petalage.*—Number of petals under normal conditions — about 20 to 25.

(5) *Color.*—(during first two days) — Inner petals at center of flower — 12C. Outer petals — 12C. Base of petals (point of attachment) — 8A. Reverse of petals — 10B. General tonality from a distance — deep yellow.

(6) *Color change.*—As bloom ages — yellow coloring becomes slightly lighter to 8C and general tonality becomes light to medium yellow coloring, after three or more days color changes to 10D.

C. Petals:

(1) *Texture.*—Thick.

(2) *Appearance.*—Inside — satiny. Outside — satiny.

(3) *Form.*—Usually rounded (not pointed) at outer edge, teardrop shape.

(4) *Arrangement.*—Shingle-like.

(5) *Petaloids in center.*—Few.

(6) *Persistence.*—Drop cleanly.

(7) *Fragrance.*—Strong for miniature, spicy-sweet.

(8) *Lasting quality.*—Average.

2. REPRODUCTIVE ORGANS

A. Stamens, filaments and anthers:

(1) *Arrangement.*—Stamens regularly arranged around styles.

(2) *Color.*—16B.

B. Pollen: Color — 17B.

C. Styles: Even length, close cluster.

D. Stigmas: Color — 159A.

E. Hips: Shape — round; size ½ to ¾ inch; seeds do not protrude.

3. PLANT

A. Form: Compact.

B. Growth: Vigorous, uniform branching. Height attained — 8 to 10 inches.

C. Foliage: Compound 5 to 7 leaflet leaves.

(1) *Size.*—Medium.

(2) *Quantity.*—Abundant.

(3) *Color.*—New foliage: Upper side — 144A. Under side — 138C. Old foliage: Upper side — 147A. Under side — 147C.

(4) *Shape.*—Pointed, oval.

(5) *Texture.*—Upper side — very glossy. Under side — matte.

(6) *Edge.*—Serrated.

(7) *Serration.*—Shallow, thin, pointed, fairly regular.

(8) *Leaf stem.*—Color — near to 138A. Under side — near to 146C.

(9) *Stipules.*—Medium long, smooth, pointed.

(10) *Resistance to disease.*—Blackspot — good. Mildew — very good.

D. Wood:

(1) *New wood.*—Color — near 144B. Bark — smooth.

(2) *Old wood.*—Color — near to 138A. Bark — smooth.

E. Thorns:

(1) *Thorns.*—Quantity — moderate. On laterals from stalk — moderate. Form — straight, pointed. Length — medium. Color (when young) — 50C. Position — irregular.

(2) *Prickles.*—None.

F. Winter Hardiness: Needs some protection in extreme climate.

I claim:

1. A new and distinct variety of rose plant of the miniature class, substantially as shown and described, characterized particularly by beautiful deep yellow blooms of strong fragrance borne primarily singly to a stem on a very compact plant of attractive foliage.

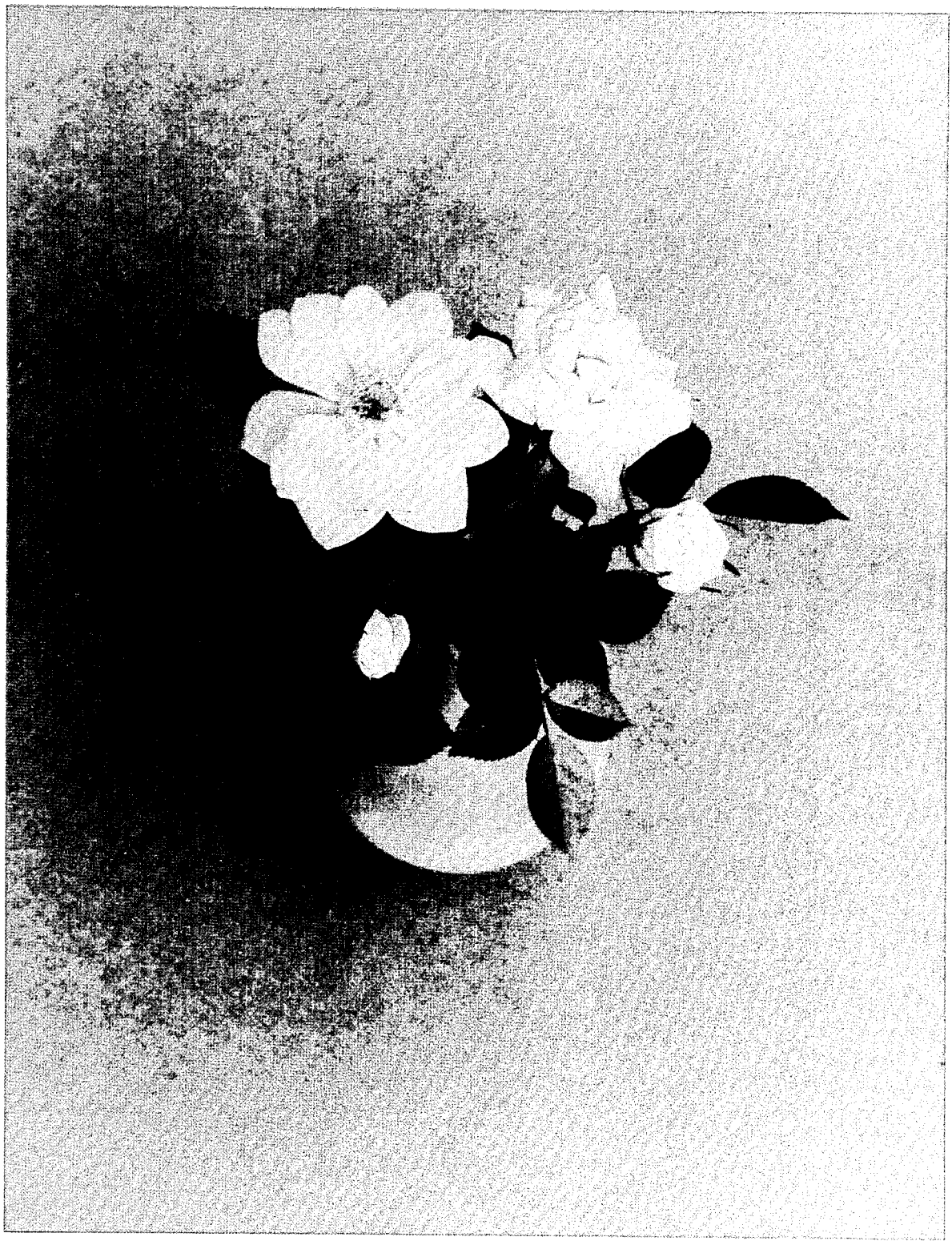

* * * * *